US010538467B2

(12) United States Patent
Quan et al.

(10) Patent No.: US 10,538,467 B2
(45) Date of Patent: Jan. 21, 2020

(54) MANUFACTURING METHOD OF 1,2-DICHLOROHEXAFLUOROCYCLOPENTENE

(71) Applicants: Beijing Yuji Science & Technology Co., Ltd., Haidian District, Beijing (CN); ZEON CORPORATION, Chiyoda-ku, Tokyo (JP)

(72) Inventors: Hengdao Quan, Beijing (CN); Dongpeng Liu, Beijing (CN); Xiaoqing Jia, Beijing (CN); Xiaomeng Zhou, Beijing (CN)

(73) Assignees: Beijing Yuji Science & Technology Co., Ltd., Haidian District (CN); ZEON CORPORATION, Chiyoda-ku, Tokyo (JP)

( * ) Notice: Subject to any disclaimer, the term of this patent is extended or adjusted under 35 U.S.C. 154(b) by 0 days.

(21) Appl. No.: 16/094,263

(22) PCT Filed: Aug. 19, 2016

(86) PCT No.: PCT/CN2016/095975
§ 371 (c)(1),
(2) Date: Oct. 17, 2018

(87) PCT Pub. No.: WO2017/181566
PCT Pub. Date: Oct. 26, 2017

(65) Prior Publication Data
US 2019/0127300 A1    May 2, 2019

(30) Foreign Application Priority Data

Apr. 22, 2016   (CN) .......................... 2016 1 0256358

(51) Int. Cl.
| C07C 17/20 | (2006.01) |
| B01J 23/26 | (2006.01) |
| B01J 23/28 | (2006.01) |
| B01J 23/30 | (2006.01) |
| B01J 37/08 | (2006.01) |
| C07C 4/22 | (2006.01) |
| C07C 17/02 | (2006.01) |

(52) U.S. Cl.
CPC ............. *C07C 17/206* (2013.01); *B01J 23/26* (2013.01); *B01J 23/28* (2013.01); *B01J 23/30* (2013.01); *B01J 37/08* (2013.01); *C07C 4/22* (2013.01); *C07C 17/02* (2013.01)

(58) Field of Classification Search
CPC ......... C07C 17/206; C07C 17/02; C07C 4/22; C07C 17/25; C07C 17/21; C07C 23/08; B01J 37/08; B01J 23/30; B01J 23/26; B01J 23/28
See application file for complete search history.

(56) References Cited

U.S. PATENT DOCUMENTS

| 3,637,479 A | 1/1972 | Rosenberg et al. |
| 3,862,253 A | 1/1975 | Cramers |

FOREIGN PATENT DOCUMENTS

| CN | 1651137 A | 8/2005 |
| CN | 101306980 A | 11/2008 |
| CN | 104907065 A | 9/2015 |
| GB | 1522489 A | 8/1978 |
| JP | 549134653 A | 12/1974 |
| JP | S5133105 B1 | 9/1976 |
| JP | S5414940 A | 2/1979 |
| JP | 2002241324 A | 8/2002 |

OTHER PUBLICATIONS

Jiang et al., method for preparing cyclopentadiene, (CN 101306980 machine translation), Nov. 2008.*
Takeo et al., method for producing perhalogenated five-membered ring compound (JP 2002241324 machine translation), Aug. 2008.*
Jian et al., fluorination catalyst, its manufacturing method and use, (CN 1651137 machine translation), Aug. 2005.*
Feb. 24, 2017, International Search Report issued in the International Patent Application No. PCT/CN2016/095975.
Oct. 29, 2019, Decision to Grant a Patent issued by the Japan Patent Office in the corresponding Japanese Patent Application No. 2019-505102.

* cited by examiner

*Primary Examiner* — Jafar F Parsa
(74) *Attorney, Agent, or Firm* — Kenja IP Law PC

(57) ABSTRACT

Disclosed is a manufacturing method of 1,2-dichlorohexafluorocyclopentene. The first reaction uses dicyclopentadiene as a starting material and nitrogen gas or another inert gas as a diluting agent in a gas-phase thermal cracking reaction to obtain cyclopentadiene. The second reaction uses cyclopentadiene as a starting material in a liquid phase chlorination reaction with chlorine gas to obtain 1,2,3,4-tetrachlorocyclopentane. The third reaction uses 1,2,3,4-tetrachlorocyclopentane as a starting material in a gas-phase chlorination and fluorination reaction with hydrogen fluoride and chlorine gas in the presence of a chromium-based catalyst to obtain 1,2-dichlorohexafluorocyclopentene. The method uses easily acquired starting material and a stable fluorination catalyst, provides a high yield for a target product, and is applicable for large-scale continuous gas-phase production of 1,2-dichlorohexafluorocyclopentene.

8 Claims, No Drawings

MANUFACTURING METHOD OF 1,2-DICHLOROHEXAFLUOROCYCLOPENTENE

The present application claims the priority of the Chinese patent application of No. 201610256358.X, titled "Manufacturing method of 1,2-dichlorohexafluorocyclopentene", filed with the State Intellectual Property Office of the P.R.C on Apr. 22, 2016, the content of which is incorporated into the present application by reference in its entirety.

TECHNICAL FIELD

The present invention relates to a manufacturing method of 1,2-dichlorohexafluorocyclopentene, in particular to a manufacturing method of 1,2-dichlorohexafluorocyclopentene by pyrolysing dicyclopentadiene to cyclopentadiene, then chlorinating the cyclopentadiene to obtain 1,2,3,4-tetrachlorocyclopentane, and finally subjecting the 1,2,3,4-tetrachlorocyclopentane to a catalytic reaction with a gas mixture of hydrogen fluoride and chlorine in a gas phase.

BACKGROUND 1,2-dichlorohexafluorocyclopentene is an important class of intermediates with high industrial value, which can be used to prepare the etchant of octafluorocyclopentene, the cleaning agent of 1,2,2,3,3,4,4,5-heptafluorocyclopentane, and the like.

Up to now, many documents have reported the methods for preparing 1,2-dichlorohexafluorocyclopentene. Mostly, synthesis is carried out by using hexachlorocyclopentadiene or octachlorocyclopentene as a starting material, wherein the fluridizer used may be $SbF_5$ (see documents U.S. Pat. No. 2,459,783 and Ind. Eng. Chem., 1947, 39 (3), 415-417), $SbF_3Cl_2$ (see J. Am. Chem. Soc., 1954, 76 (2), 610-612), $SbF_xCl_{5-x}$ (0<x<5) (see J. Am. Chem. Soc., 1945, 67, 1235-1237), or a mixture of $SbF_3$ and $SbF_1Cl_2$ (see Journal Indian Chem. Soc., 1953, 30, 525-528). The synthesis may also be carried out by using anhydrous hydrogen fluoride as a fluridizer in the presence of fluorination catalysts such as $SbCl_5$ catalysts (see documents WO9743233, WO9600707 and U.S. Pat. No. 6,218,586) or catalysts containing bismuth or iron (see document U.S. Pat. No. 5,180,861).

The above preparation process has the following disadvantages: first, the starting materials are difficult to obtain; secondly, when the fluridizer is a fluorine-containing and/or chlorine-containing antimony compound, such a fluridizer is highly corrosive and easily hydrolyzed to release hydrogen fluoride or hydrogen chloride gas, which makes it difficult to handle and control in use; when the fluridizer is anhydrous hydrogen fluoride, the fluorination catalyst has low activity and is easily deactivated.

SUMMARY OF THE INVENTION

The technical problem to be solved by the present invention is to address the deficiencies mentioned in the background, and to provide a method for preparing 1,2-dichlorohexafluorocyclopentene suitable for large-scale production, by using raw materials that are easy to obtain, and fluorination catalysts with high activity and stability.

Disclosed is a method for preparing 1,2-dichlorohexafluorocyclopentene, comprising: in step one, pyrolysing dicyclopentadiene, as raw material, to obtain cyclopentadiene, with nitrogen or other inert gas as a diluent; in step two, subjecting cyclopentadiene, as raw material, to a chlorination reaction in a liquid phase with chlorine to obtain 1,2,3,4-tetrachlorocyclopentane; and in step three, subjecting 1,2,3,4-tetrachlorocyclopentane, as raw material, to a chlorofluorination reaction with hydrogen fluoride and chlorine in a gas phase in the presence of a chromium-based catalyst to obtain 1,2-dichlorohexafluorocyclopentene.

In the method, the principal effect of the diluent is to prevent the materials from generating a large amount of polymer as being in the reactor at a high temperature for a long time. Besides nitrogen, other inert gases such as argon gas, helium gas, etc., which do not react with dicyclopentadiene and cyclopentadiene, can also be used as the diluent.

The chromium-based catalyst is prepared by calcinating a catalyst precursor at a high temperature. The catalyst precursor is made of a mixture of a trivalent chromium compound and a metal powder in a mass percentage ratio of 95% to 99.9%:0.1% to 5%. That is to say, based on the total mass of the catalyst precursor, the trivalent chromium compound represents 95% to 99.9% by mass, and the metal powder represents 0.1% to 5% by mass.

In the method, the trivalent chromium compound is chromium hemitrioxide or chromium hydroxide, and the metal powder is one or more of tungsten powder, molybdenum powder, and indium powder.

The calcination at a high temperature is carried out at 300° C. to 500° C. for 6 to 15 hours under a nitrogen atmosphere.

The chromium-based catalyst needs to be activated at 60° C. to 450° C. for 6 h to 15 h in a gaseous mixture of nitrogen and hydrogen fluoride in a molar ratio of 10:1 before use.

In step one, the molar ratio of the diluent to dicyclopentadiene is 1:0.5 to 3, the reaction pressure is 0.1 MPa to 1.5 MPa, the reaction temperature is 300° C. to 450° C., and the contact time is 5 s to 30 s.

In step two, the molar ratio of chlorine to cyclopentadiene is 1 to 3:1, the reaction temperature is 0° C. to 40° C., and the reaction time is 1 h to 10 h (hours).

In step three, the molar ratio of 1,2,3,4-tetrachlorocyclopentane, hydrogen fluoride and chlorine is 1:5 to 20:5, the reaction pressure is 0.1 MPa to 1.5 MPa, the reaction temperature is 300° C. to 500° C., and the contact time is 2 s to 30 s.

The present invention uses dicyclopentadiene as starting material, and provides 1,2-dichlorohexafluorocyclopentene by pyrolysis in a gas phase, chlorination in a liquid phase and catalytic chlorofluorination in a gas phase. The main reactions are as follows:

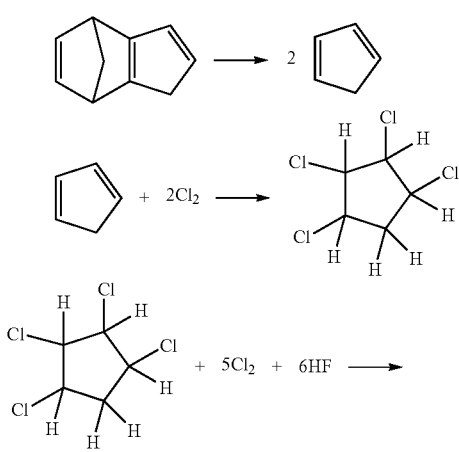

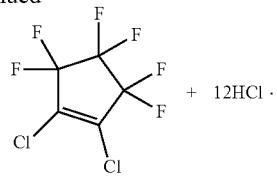 + 12HCl

The reactor type of the present invention is not critical. The reactors used in steps one and three may be a tubular reactor, a fluidized bed reactor and the like, as well as an adiabatic or an isothermal reactor, preferably a tubular reactor. Step two can be carried out in a reactor made of glass, stainless steel or polytetrafluoroethylene, preferably a glass autoclave.

The precursor of the chromium-based catalyst used in the present invention is made of a mixture of a trivalent chromium compound and a metal powder in a mass percentage ratio of 95% to 99.9%:0.1% to 5%, wherein the trivalent chromium compound is chromium hemitrioxide or chromium hydroxide, preferably chromium hydroxide, the metal powder is one or more of tungsten powder, molybdenum powder, and indium powder. The chromium-based catalyst (fluorination catalyst) is prepared by mixing a trivalent chromium compound and a metal powder uniformly in the mass percentage above, and shaping the mixture under pressure to obtain a catalyst precursor; calcinating the obtained catalyst precursor at 300° C. to 500° C. for 6 h to 15 h under a nitrogen atmosphere; then activating the calcinated catalyst precursor at 60° C. to 450° C. for 6 h to 15 h in a mixing atmosphere composed of hydrogen fluoride and nitrogen at a molar ratio of 1:10, to obtain the chromium-based catalyst. In addition to the above chromium-based catalysts, any other known fluorination catalysts can be used in the present invention, for example, chromium oxide, chromium fluoride, fluorinated chromium oxide, aluminum fluoride, fluorinated alumina, chromium oxide loaded on activated carbon, chromium oxide loaded on aluminum fluoride, chromium oxide loaded on magnesium fluoride, chromium oxide containing various metals (such as Zn, Co, Ni, Ge, In, etc.), and antimony pentachloride loaded on activated carbon or titanium tetrachloride loaded on activated carbon, etc. The reaction conditions are various by using various fluorination catalysts, including reaction temperature, reaction pressure, contact time, and material molar ratios, resulting in various yields of 1,2-dichlorohexafluorocyclopentene.

A mixing method is used to prepare a chromium-based catalyst in the present invention, wherein a trivalent chromium compound and a metal powder are mixed in a certain ratio to obtain a catalyst precursor; during the calcination of the catalyst precursor at a high temperature, the trivalent chromium compound presents in the form of chromium oxide, while the metal powder retains as an elementary substance; then activation is performed in the mixture composed of nitrogen and hydrogen fluoride gas, and the metal powder such as tungsten powder, molybdenum powder and indium powder is reacted with hydrogen fluoride gas to form fluoride, after the chromium oxide is fluorinated to chromium fluoride and no steam is generated. The generated fluorides (such as tungsten fluoride and molybdenum fluoride) mostly leave the catalyst structure in a gas form, which not only provides pores for catalyst, but also increases the specific surface area and pore volume of catalyst, resulting in increased activity of the catalyst. Meanwhile, the metallic element which is not lost is mainly retained in the catalyst in the form of elementary substance or a small amount of hexafluoride, so that the carbon deposition of the catalyst at a high temperature can be effectively inhibited. As a whole, the fluorination catalyst prepared by the above method has a high service temperature and a high catalytic activity.

Preferably, the reaction conditions of the present invention are as follows: in step one, the molar ratio of diluent to dicyclopentadiene is 1:1 to 2, the reaction temperature is 330° C. to 370° C., the reaction pressure is 0.1 MPa to 1.5 MPa, and the contact time is 10 s to 20 s; in step two, the molar ratio of chlorine to cyclopentadiene is 1.5 to 1:1, the reaction temperature is 20° C. to 30° C., the reaction time is 3 h to 7 h; in step three, the molar ratio of 1,2,3,4-tetrachlorocyclopentane, hydrogen fluoride and chlorine is 1:10 to 15:5, the reaction pressure is 0.1 MPa to 1.5 MPa, the reaction temperature is 370° C. to 450° C., and the contact time is 10 s to 20 s.

The method of the invention is advantageous in terms of easy availability of raw materials, high activity and high stability of the chromium-based catalyst, and suitability for large-scale production of 1,2-dichlorohexafluorocyclopentene.

DETAILS OF THE INVENTION

In order to make the objects, technical solutions, and advantages of the present invention more comprehensible, the present invention will be further described in detail below by way of examples. It is apparent that the described examples are only a part of the examples of the invention, and not all of them. Based on the examples in the present application, any other examples obtained by the ordinary skilled person in the art without creative work are within the protection scope of the present invention.

Example 1

30 ml of inert alumina was charged into a tubular reactor made of Inconel alloy with an inner diameter of ½ inch and a length of 30 cm. The reactor was heated to 370° C., and nitrogen and dicyclopentadiene were simultaneously introduced into the reactor. The molar ratio of nitrogen to dicyclopentadiene was controlled to be 1:1.5, the contact time was controlled to be 15 seconds, and the reaction pressure was controlled to be 0.1 MPa. The reaction product was cooled in an ice bath at 0° C. to obtain cyclopentadiene. The yield of cyclopentadiene was determined by gas chromatography, and the results are shown in Table 1.

The conditions for the gas chromatography include: Analytical instruments: chromatographic instrument GC-930 from Shanghai Haixin Group Co., Ltd., hydrogen flame detector, the column of capillary column $Al_2O_3$/S "50 m×0.320 mm×0.25 µm" (manufactured by the Chromatography Technology Research and Development Center, Lanzhou Institute of Chemical Physics, Chinese Academy of Sciences).

Gas Chromatographic Analysis Method: high purity nitrogen (99.999%) was used as a carrier gas. The detection conditions are as follows: the temperature in vaporization chamber was 250° C., the temperature of auxiliary furnace 2 was 250° C., the temperature of detector was 250° C., the initial temperature of column furnace was 40° C. for 10 minutes, the heating rate was 15° C./min, the final temperature was 230° C. for 3 minutes, and the split ratio was 20:1.

It should be noted that the yields of the products were determined by the same gas chromatographic conditions as in Example 1 in the following examples.

Example 2

The same operation as in Example 1 was performed, except that the reaction temperature was 300° C., and the results are shown in Table 1.

Example 3

The same operation as in Example 1 was performed, except that the reaction temperature was 330° C., and the results are shown in Table 1.

Example 4

The same operation as in Example 1 was performed, except that the reaction temperature was 410° C., and the results are shown in Table 1.

Example 5

The same operation as in Example 1 was performed, except that the reaction temperature was 450° C., and the results are shown in Table 1.

Example 6

The same operation as in Example 1 was performed, except that the contact time was 2 s, and the results are shown in Table 1.

Example 7

The same operation as in Example 1 was performed, except that the contact time was 10 s, and the results are shown in Table 1.

Example 8

The same operation as in Example 1 was performed, except that the contact time was 20 s, and the results are shown in Table 1.

Example 9

The same operation as in Example 1 was performed, except that the contact time was 30 s, and the results are shown in Table 1.

Example 10

The same operation as in Example 1 was performed, except that the molar ratio of nitrogen to dicyclopentadiene was 1:0.5, and the results are shown in Table 1.

Example 11

The same operation as in Example 1 was performed, except that the molar ratio of nitrogen to dicyclopentadiene was 1:1, the results are shown in Table 1.

Example 12

The same operation as in Example 1 was performed, except that the molar ratio of nitrogen to dicyclopentadiene was 1:2, and the results are shown in Table 1.

Example 13

The same operation as in Example 1 was performed, except that the molar ratio of nitrogen to dicyclopentadiene was 1:3, and the results are shown in Table 1.

Example 14

The same operation as in Example 1 was performed, except that the reaction pressure was 0.5 MPa, and the results are shown in Table 1.

Example 15

The same operation as in Example 1 was performed, except that the reaction pressure was 1.0 MPa, and the results are shown in Table 1.

Example 16

The same operation as in Example 1 was performed, except that the reaction pressure was 1.5 MPa, and the results are shown in Table 1.

TABLE 1

| Examples | Temperature/ °C. | Pressure/ MPa | Contact time/s | Molar ratio of $N_2:C_{10}H_{20}$ | cyclopentadiene Yield/% |
|---|---|---|---|---|---|
| Example 1 | 370 | 0.1 | 15 | 1:1.5 | 99.4 |
| Example 2 | 300 | 0.1 | 15 | 1:1.5 | 87.9 |
| Example 3 | 330 | 0.1 | 15 | 1:1.5 | 90.9 |
| Example 4 | 410 | 0.1 | 15 | 1:1.5 | 79.3 |
| Example 5 | 450 | 0.1 | 15 | 1:1.5 | 68.5 |
| Example 6 | 370 | 0.1 | 2 | 1:1.5 | 39.2 |
| Example 7 | 370 | 0.1 | 10 | 1:1.5 | 83.7 |
| Example 8 | 370 | 0.1 | 20 | 1:1.5 | 92.6 |
| Example 9 | 370 | 0.1 | 30 | 1:1.5 | 80.4 |
| Example 10 | 370 | 0.1 | 15 | 1:0.5 | 95.1 |
| Example 11 | 370 | 0.1 | 15 | 1:1 | 96.4 |
| Example 12 | 370 | 0.1 | 15 | 1:2 | 95.2 |
| Example 13 | 370 | 0.1 | 15 | 1:3 | 75.3 |
| Example 14 | 370 | 0.5 | 15 | 1:1.5 | 90.1 |
| Example 15 | 370 | 1.0 | 15 | 1:1.5 | 83.6 |
| Example 16 | 370 | 1.5 | 15 | 1:1.5 | 59.8 |

Example 17

Cyclopentadiene and chlorine were simultaneously added into the autoclave; the molar ratio of cyclopentadiene to chlorine was controlled to 1:1.5, the temperature in autoclave was controlled to 20° C., and the reaction time was controlled to 5 h. The product was washed with water and alkali, and then dried with 4A molecular sieves, to obtain 1,2,3,4-tetrachlorocyclopentane; the yield of 1,2,3,4-tetrachlorocyclopentane was determined by gas chromatography, and the results are shown in Table 2.

Example 18

The same operation as in Example 17 was performed, except that the molar ratio of cyclopentadiene to chlorine was 1:1, and the results are shown in Table 2.

Example 19

The same operation as in Example 17 was performed, except that the molar ratio of cyclopentadiene to chlorine was 1:2, and the results are shown in Table 2.

Example 20

The same operation as in Example 17 was performed, except that the molar ratio of cyclopentadiene to chlorine was 1:3, and the results are shown in Table 2.

Example 21

The same operation as in Example 17 was performed, except that the reaction temperature was 0° C. and the reaction time was 10 h, and the results are shown in Table 2.

Example 22

The same operation as in Example 17 was performed, except that the reaction temperature was 10° C. and the reaction time was 7 h, and the results are shown in Table 2.

Example 23

The same operation as in Example 17 was performed, except that the reaction temperature was 30° C. and the reaction time was 3 h, and the results are shown in Table 2.

Example 24

The same operation as in Example 17 was performed, except that the reaction temperature was 40° C. and the reaction time was 1 h, and the results are shown in Table 2.

TABLE 2

| Examples | Reaction Temperature/ °C. | Reaction Time/h | Molar ratio of $C_5H_6$:$Cl_2$ | 1,2,3,4-tetrachlorocyclopentane Yield/% |
|---|---|---|---|---|
| Example 17 | 20 | 5 | 1:1.5 | 98.2 |
| Example 18 | 20 | 5 | 1:1 | 78.2 |
| Example 19 | 20 | 5 | 1:2 | 93.3 |
| Example 20 | 20 | 5 | 1:3 | 90.6 |
| Example 21 | 0 | 10 | 1:1.5 | 73.8 |
| Example 22 | 10 | 7 | 1:1.5 | 82.5 |
| Example 23 | 30 | 3 | 1:1.5 | 93.4 |
| Example 24 | 40 | 1 | 1:1.5 | 90.2 |

Methods for preparing chromium-based catalysts involved in Examples 25 to 28 are as follows.

The chromium nitrate was dissolved in water, added with a precipitant of aqueous ammonia at 60° C. The resulted solution was adjusted to pH 7.5 to 8.5, so that the precipitate was fully separate out under stirring. The formed slurry was filtered and washed with deionized water until it was neutral, and then dried at 150° C. for 12 hours to obtain chromium hydroxide.

The obtained chromium hydroxide and metal powder (the metal powder is tungsten powder, molybdenum powder and/or indium powder) were mixed uniformly in the mass percentage ratio of 95% to 99.9%:0.1% to 5%, and shaped under pressure to obtain a catalyst precursor. Then, the catalyst precursor was calcinated at 450° C. for 10 hours under a nitrogen atmosphere, and then activated at 60° C. to 450° C. for 12 hours under a mixing atmosphere composed of hydrogen fluoride gas and nitrogen at a molar ratio of 1:10, to obtain a chromium-based catalyst.

Example 25

10 ml of a chromium-based catalyst was charged into a tubular reactor made of Inconel alloy with an inner diameter of ½ inch and a length of 30 cm. The chromium-based catalyst precursor was prepared by mixing chromium hydroxide and tungsten powder in the mass percentage ratio of 97%:3% and shaping the mixture under pressure, with the temperature for activation of 300° C. The reactor was heated to 370° C., and anhydrous hydrogen fluoride, 1,2,3,4-tetrachlorocyclopentane and chlorine were simultaneously introduced into the reactor. The molar ratio of anhydrous hydrogen fluoride, 1,2,3,4-tetrachlorocyclopentane and chlorine was controlled to 12:1:5, the contact time was controlled to 15 seconds, and the reaction pressure was controlled to 0.1 MPa. After 20 hours of reaction, the reaction product was washed with water and alkali, and separated to obtain an organic material. The organic material was dried to remove water, so as to obtain a product. The product was characterized by gas chromatography-mass spectrometry (GC-MS) technique and nuclear magnetic resonance ($^{19}F$ NMR) as follows:

GC-MS:

Instruments and conditions: GC-MS-QP2010 Ultra (Shimadzu), column: DB-5 with an inner diameter of 0.25 mm and a length of 30 m (J&W Scientific Inc.); programmed temperature: 40° C. for 4 min; raised to 230° C. at a rate of 10° C./min, for 5 min; the inlet temperature and detector temperature were maintained at 200° C., and the carrier gas He was maintained at 10 mL/min.

Test Results:

m/z:244 ($M^+$); 225 ($M^+$-F); 209 ($M^+$-Cl); 194 ($M^+$-$CF_2$); 175 ($M^+$-$CF_3$); 159 ($M^+$-$CF_2Cl$); 155 ($M^+$-$FCl_2$); 140 ($M^+$-$CF_3Cl$); 125 ($M^+$-$CF_2Cl_2$); 109 ($M^+$-$C_2F_4Cl$); 90 ($M^+$-$C_2F_5Cl$); 85 ($M^+$-$C_4F_4Cl$); 69 ($M^+$-$C_4F_3Cl_2$); 55 ($M^+$-$C_2F_5Cl_2$); 31 ($M^+$-$C_4F_5Cl_2$); 18 ($M^+$-$C_5F_5Cl_2$).

$^{19}F$ NMR: Fluorine spectrum ($^{19}F$ NMR) of the product was tested at 25° C., the internal standard was $CFCl_3$, and the solvent was $CDCl_3$; the test results: δ−113.75 (dt, 4F); −129.73 (ddt, 2F).

The product of Example 25 was determined to be 1,2-dichlorohexafluorocyclopentene by the above-mentioned GC-MS and NMR data; the yield of 1,2-dichlorohexafluorocyclopentene was determined by gas chromatography, and the results are shown in the Table 3.

Example 26

The same operation as in Example 25 was performed, except that the chromium-based catalyst precursor was prepared by uniformly mixing chromium hydroxide and indium powder in the mass percentage ratio of 97%:3% and shaping the mixture under pressure, and the reaction temperature was 300° C. The results are shown in Table 3.

Example 27

The same operation as in Example 25 was performed, except that the chromium-based catalyst precursor was prepared by uniformly mixing chromium hydroxide and tungsten powder in the mass percentage ratio of 99.9%:0.1% and shaping the mixture under pressure, and the reaction temperature was 330° C. The results are shown in Table 3.

Example 28

The same operation as in Example 25 was performed, except that the tungsten powder in the chromium-based catalyst precursor was replaced by molybdenum powder, the temperature for activation was 60° C. and the reaction temperature was 410° C. The results are shown in Table 3.

TABLE 3

| Examples | Temperature/ °C. | Pressure/ MPa | Contact time/s | Molar ratio of HF:C$_5$Cl$_4$H$_6$:Cl$_2$ | 1,2-dichloro-hexafluoro-cyclopentene Yield/% |
|---|---|---|---|---|---|
| Example 25 | 370 | 0.1 | 15 | 12:1:5 | 48.1 |
| Example 26 | 300 | 0.1 | 15 | 12:1:5 | 4.3 |
| Example 27 | 330 | 0.1 | 15 | 12:1:5 | 10.9 |
| Example 28 | 410 | 0.1 | 15 | 12:1:5 | 39.2 |

The above is only the preferred embodiment of the present invention, and is not intended to limit the present invention. Any modifications, equivalents, improvements, etc., which are made within the spirit and principles of the present invention, should be included within the protection scope of the present invention.

The invention claimed is:

1. A method for preparing 1,2 dichlorohexafluorocyclopentene, comprising:

in step one: pyrolysing dicyclopentadiene, as raw material, to obtain cyclopentadiene, with nitrogen or other inert gas as a diluent in a molar ratio of the diluent to dicyclopentadiene of 1:0.5 to 3, wherein the pyrolysing is at a reaction pressure of 0.1 MPa to 1.5 MPa, a reaction temperature of 300° C. to 450° C. and a contact time of 5 s to 30 s;

in step two: subjecting cyclopentadiene, as raw material, to a chlorination reaction in a liquid phase with chlorine to obtain 1,2,3,4-tetrachlorocyclopentane, in a molar ratio of chlorine to cyclopentadiene of 1 to 3:1, wherein the chlorination reaction is at a reaction temperature of 0° C. to 40° C., and a reaction time of 1 h to 10 h;

in step three: subjecting 1,2,3,4-tetrachlorocyclopentane, as raw material, to a chlorofluorination reaction with hydrogen fluoride and chlorine in a gas phase in the presence of a chromium-based catalyst to obtain 1,2-dichlorohexafluorocyclopentene, in a molar ratio of 1,2,3,4-tetrachlorocyclopentane, hydrogen fluoride and chlorine of 1:5 to 20:5, wherein the chlorofluorination reaction is at a reaction pressure of 0.1 MPa to 1.5 MPa, a reaction temperature of 370° C. to 450° C. and a contact time of 2 s to 30 s.

2. The method according to claim 1, wherein the chromium-based catalyst is prepared by calcinating a catalyst precursor at a high temperature, the catalyst precursor is a mixture of a trivalent chromium compound and a metal powder, and based on the total mass of the catalyst precursor, the trivalent chromium compound represents 95% to 99.9% by mass, and the metal powder represents 0.1% to 5% by mass.

3. The method according to claim 2, wherein the trivalent chromium compound is chromium hemitrioxide or chromium hydroxide, and the metal powder is one or more of tungsten powder, molybdenum powder, and indium powder.

4. The method according to claim 2, wherein the calcinating at a high temperature is performed at 300° C. to 500° C. for 6 h to 15 h under a nitrogen atmosphere.

5. The method according to claim 4, wherein the chromium-based catalyst is activated at 60° C. to 450° C. in a gas mixture of a nitrogen and a hydrogen fluoride gas in a molar ratio of 10:1 for 6 h to 15 h before use.

6. The method according to claim 1, wherein in step one, the molar ratio of the diluent to dicyclopentadiene is 1:1 to 2, the reaction temperature is 330° C. to 370° C., the reaction pressure is 0.1 MPa to 1.5 MPa, and the contact time is 10 s to 20 s.

7. The method according to claim 1, wherein in step two, the molar ratio of chlorine to cyclopentadiene is 1.5 to 1:1, the reaction temperature is 20° C. to 30° C., and the reaction time is 3 h to 7 h.

8. The method according to claim 1, wherein in step three, the molar ratio of 1,2,3,4-tetrachlorocyclopentane, hydrogen fluoride and chlorine is 1:10 to 15:5, the reaction pressure is 0.1 MPa to 1.5 MPa, and the contact time is 10 s to 20 s.

* * * * *

UNITED STATES PATENT AND TRADEMARK OFFICE
CERTIFICATE OF CORRECTION

PATENT NO. : 10,538,467 B2
APPLICATION NO. : 16/094263
DATED : January 21, 2020
INVENTOR(S) : Hengdao Quan et al.

It is certified that error appears in the above-identified patent and that said Letters Patent is hereby corrected as shown below:

On the Title Page

Item (56) FOREIGN PATENT DOCUMENTS Line 5, "JP 549134653 A" should read "JP S49134653 A".

In the Specification

Column 2, Line 50, please delete "  " and insert --  --.

Signed and Sealed this
Eighteenth Day of August, 2020

Andrei Iancu
*Director of the United States Patent and Trademark Office*